(12) United States Patent
Ikeda et al.

(10) Patent No.: US 10,993,701 B2
(45) Date of Patent: May 4, 2021

(54) ULTRASONIC IMAGING DEVICE

(71) Applicant: Hitachi, Ltd., Tokyo (JP)

(72) Inventors: Teiichiro Ikeda, Tokyo (JP); Masanori Hisatsu, Tokyo (JP); Chizue Ishihara, Tokyo (JP); Mayumi Suzuki, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 382 days.

(21) Appl. No.: 15/755,353

(22) PCT Filed: Jul. 25, 2016

(86) PCT No.: PCT/JP2016/071688
§ 371 (c)(1),
(2) Date: Feb. 26, 2018

(87) PCT Pub. No.: WO2017/047232
PCT Pub. Date: Mar. 23, 2017

(65) Prior Publication Data
US 2018/0242953 A1    Aug. 30, 2018

(30) Foreign Application Priority Data

Sep. 16, 2015  (JP) .............................. JP2015-183367

(51) Int. Cl.
*A61B 8/08*    (2006.01)
*G01S 7/52*    (2006.01)
(Continued)

(52) U.S. Cl.
CPC .......... *A61B 8/5269* (2013.01); *A61B 8/5207* (2013.01); *G01S 7/52047* (2013.01);
(Continued)

(58) Field of Classification Search
CPC ............ G01S 7/52047; G01S 15/8997; G01S 15/8927
See application file for complete search history.

(56) References Cited

U.S. PATENT DOCUMENTS 6,432,054 B1 * 8/2002 Ustuner .............. G01S 7/52046
600/437
7,887,486 B2 * 2/2011 Ustuner ............... A61B 8/5269
600/443
(Continued)

FOREIGN PATENT DOCUMENTS

| JP | 2008-220652 A | 9/2008 |
|---|---|---|
| JP | 2012-228513 A | 11/2012 |
| WO | WO 2015/025654 A1 | 2/2015 |

OTHER PUBLICATIONS

International Preliminary Report on Patentability (PCT/IB/338 & PCT/IB/373) issued in PCT Application No. PCT/JP2016/071688 dated Mar. 29, 2018, including English translation of document C2 (Japanese-language Written Opinion (PCT/ISA/237)) previously filed on Feb. 26, 2018 (six pages).

(Continued)

*Primary Examiner* — Amanda Lauritzen Moher
*Assistant Examiner* — Jillian K. McGough
(74) *Attorney, Agent, or Firm* — Crowell & Moring LLP

(57) ABSTRACT

A clutter reduction effect using adaptive beam forming is uniformly obtained with respect to the entire image even in an imaging condition in which the number of bundled signals is greatly distributed in an ultrasonic image. A received signal processing unit includes a summing unit that bundles the plurality of received signals for a predetermined imaging point or a plurality of signals obtained by processing the received signals, and a weighting unit that obtains a coherence value among the plurality of signals summed in the summing unit, and weights the plurality of signals before (Continued)

being summed in the summing unit or a signal obtained through summing in the summing unit, with a weight corresponding to the coherence value. The weighting unit weights the coherence value nonlinearly in a predetermined direction in the subject, and weights the plurality of signals before being summed in the summing unit or the signal obtained through summing in the summing unit by using the nonlinearly weighted coherence value.

13 Claims, 15 Drawing Sheets

(51) Int. Cl.
*G01S 15/89* (2006.01)
*A61B 8/14* (2006.01)

(52) U.S. Cl.
CPC ...... *G01S 15/8927* (2013.01); *G01S 15/8997* (2013.01); *A61B 8/14* (2013.01)

(56) References Cited

U.S. PATENT DOCUMENTS

| | | | |
|---|---|---|---|
| 2006/0173313 A1* | 8/2006 | Liu | G01S 7/52046 600/437 |
| 2009/0069692 A1* | 3/2009 | Cooley | G01S 7/52095 600/459 |
| 2012/0269408 A1 | 10/2012 | Kim et al. | |
| 2012/0277589 A1* | 11/2012 | Katou | G10K 11/341 600/443 |
| 2012/0296215 A1* | 11/2012 | Brown | A61B 8/5269 600/447 |
| 2013/0109971 A1* | 5/2013 | Dahl | A61B 8/08 600/447 |
| 2014/0024943 A1* | 1/2014 | Nicolas | G01S 15/8959 600/447 |
| 2015/0164475 A1* | 6/2015 | Kuga | A61B 8/5238 600/443 |
| 2015/0272551 A1* | 10/2015 | Jung | A61B 8/5223 600/443 |
| 2015/0359512 A1* | 12/2015 | Boctor | A61B 8/469 600/444 |
| 2015/0366542 A1* | 12/2015 | Brown | A61B 8/5269 600/447 |
| 2016/0095520 A1* | 4/2016 | Zhang | A61B 8/13 600/407 |
| 2017/0023668 A1* | 1/2017 | Chang | G01S 7/52095 600/459 |

OTHER PUBLICATIONS

International Search Report (PCT/ISA/210) issued in PCT Application No. PCT/JP2016/071688 dated Sep. 6, 2016 with English translation (Three (3) pages).
Japanese-language Written Opinion (PCT/ISA/237) issued in PCT Application No. PCT/JP2016/071688 dated Sep. 6, 2016 (Three (3) pages).

* cited by examiner

[Fig. 1]
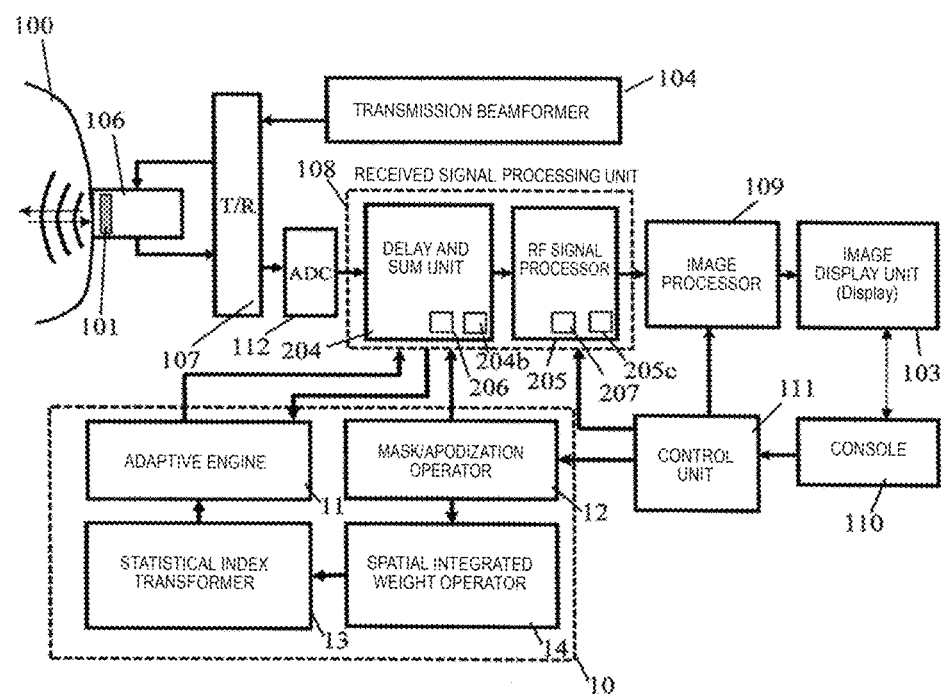

[Fig. 2]
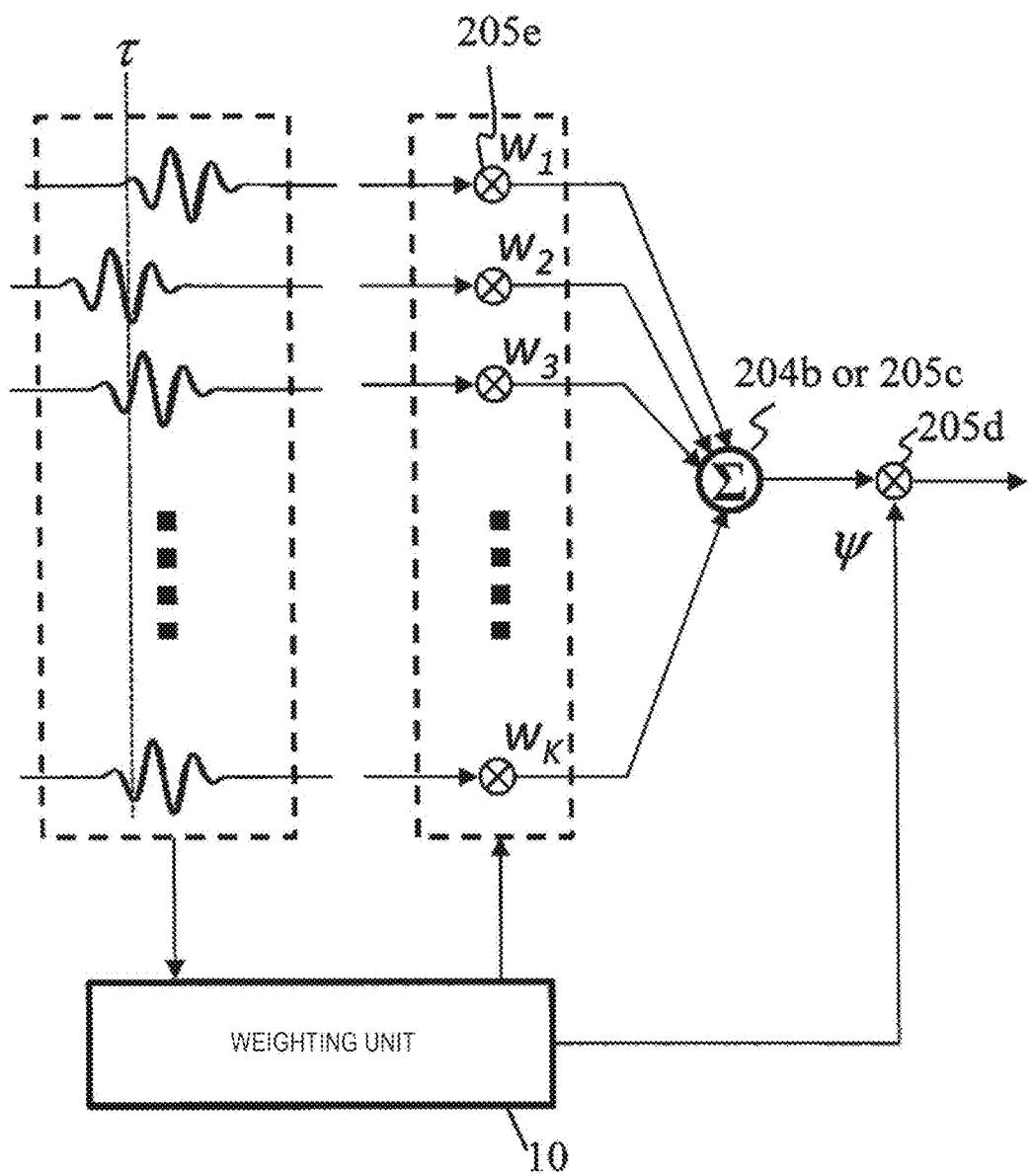

[Fig. 3]
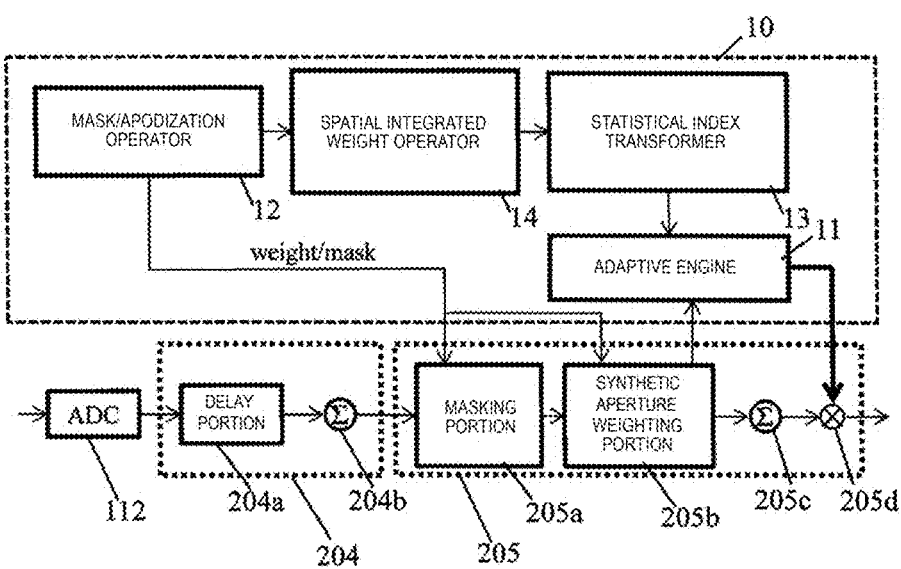

[Fig. 4]
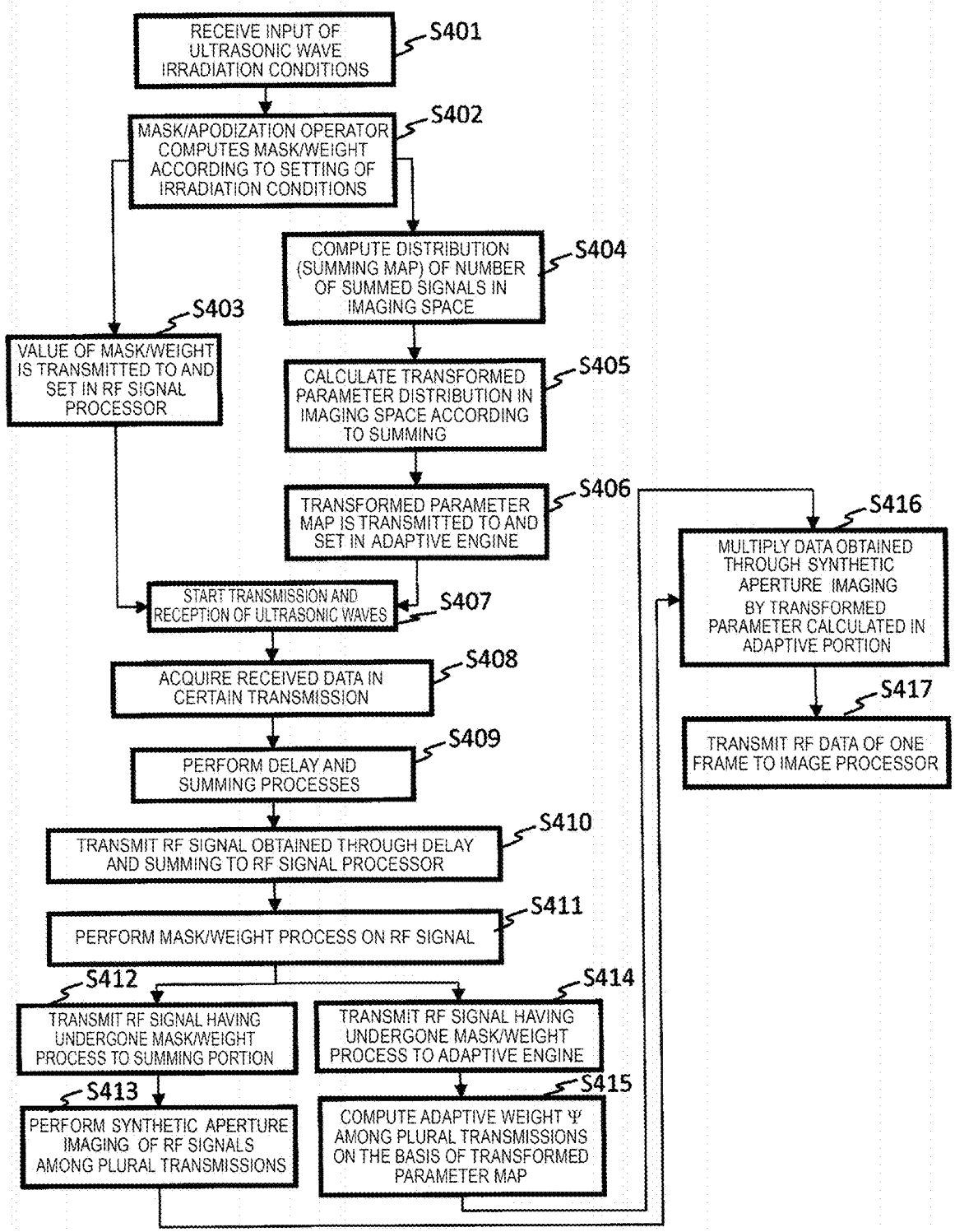

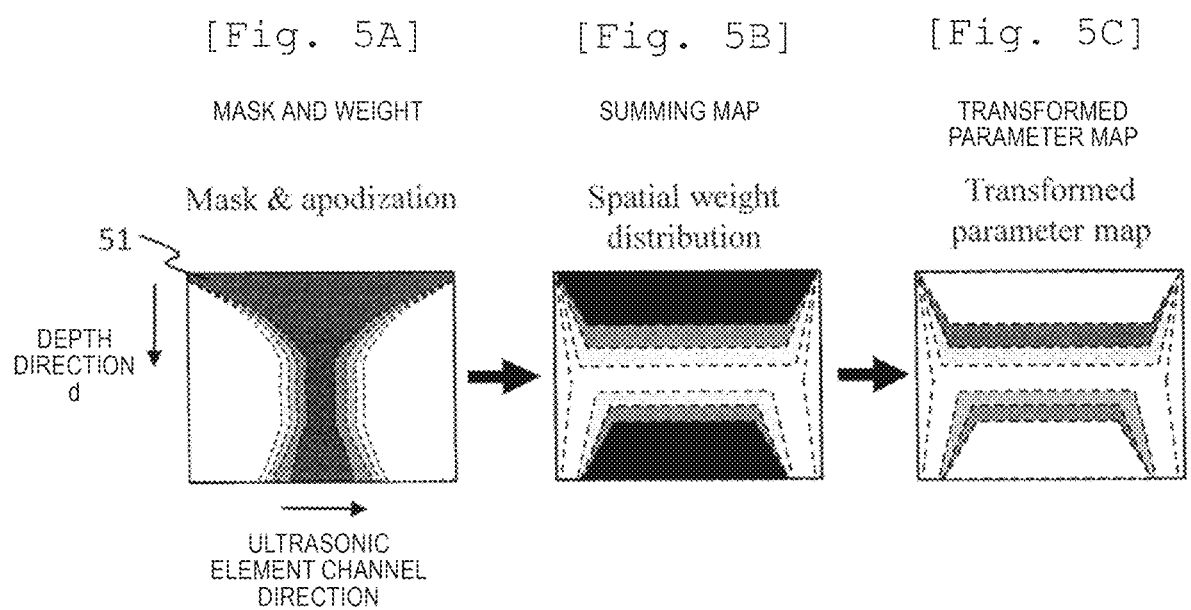

[Fig. 6A]
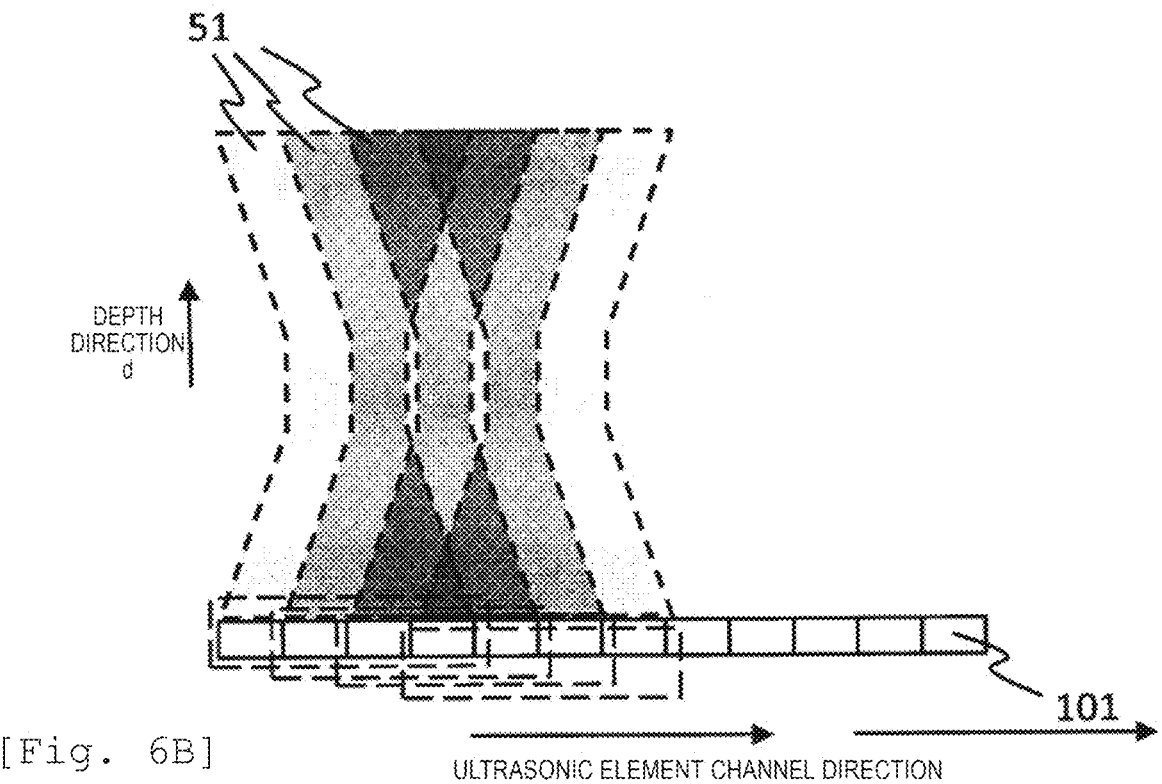
[Fig. 6B]
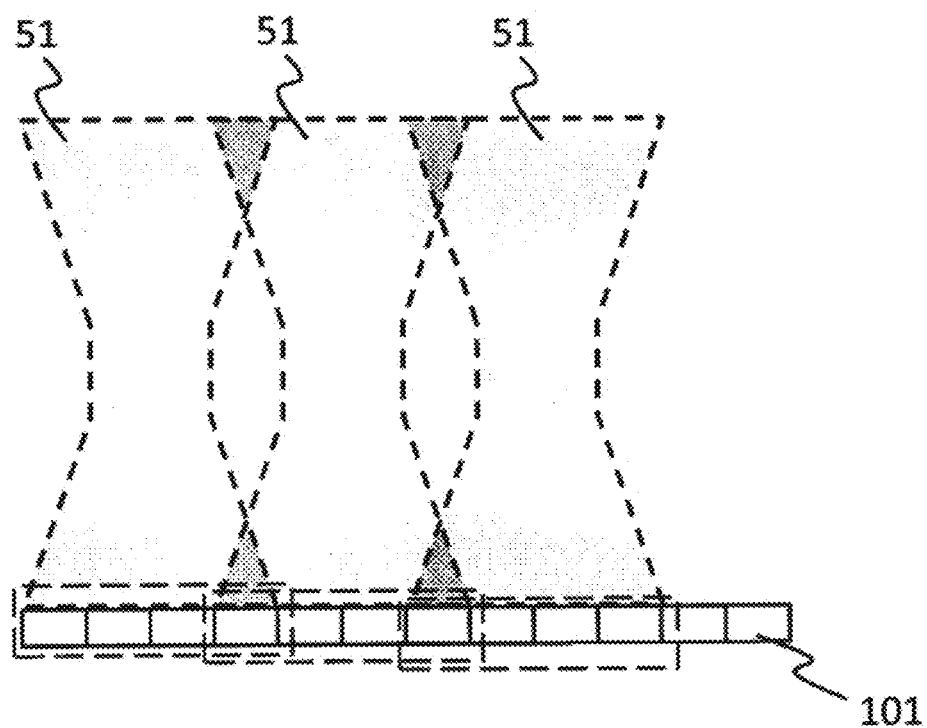

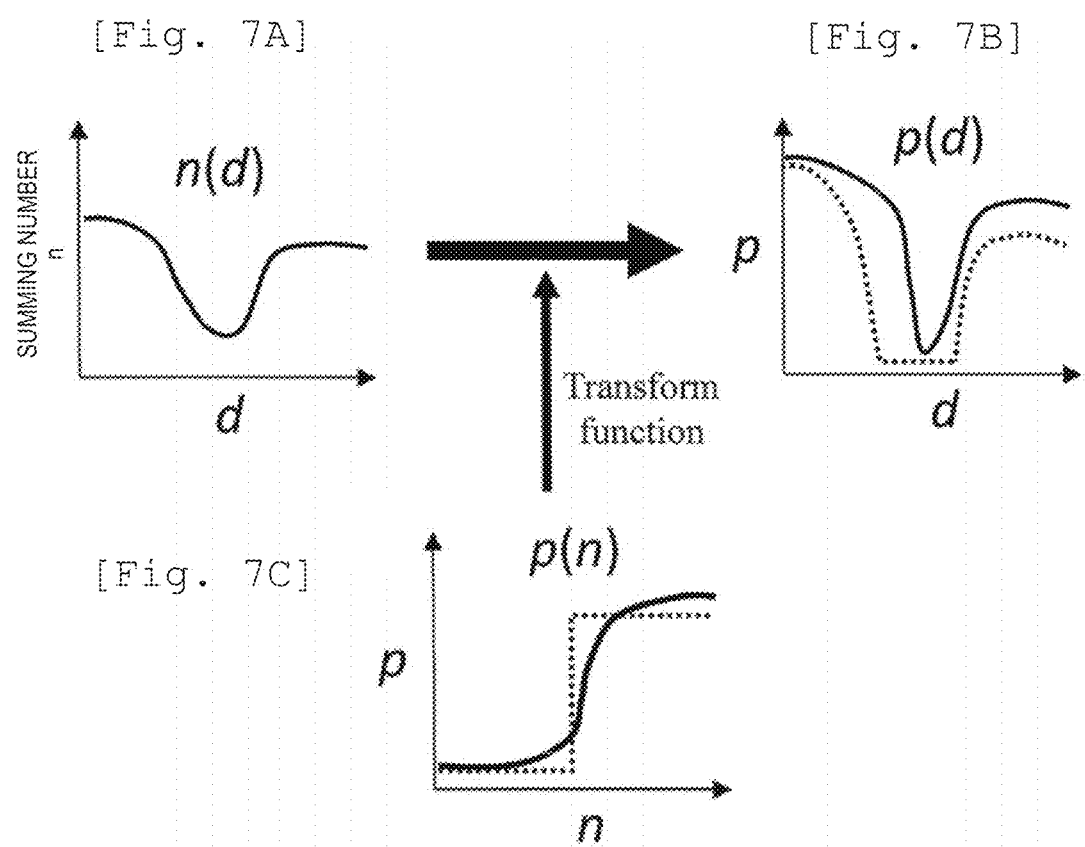

[Fig. 8]
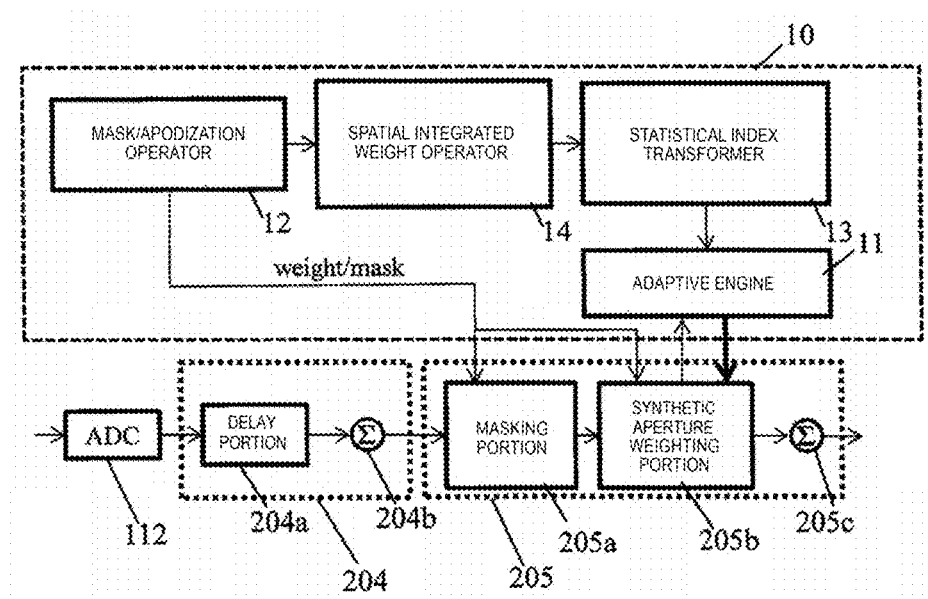

[Fig. 9]
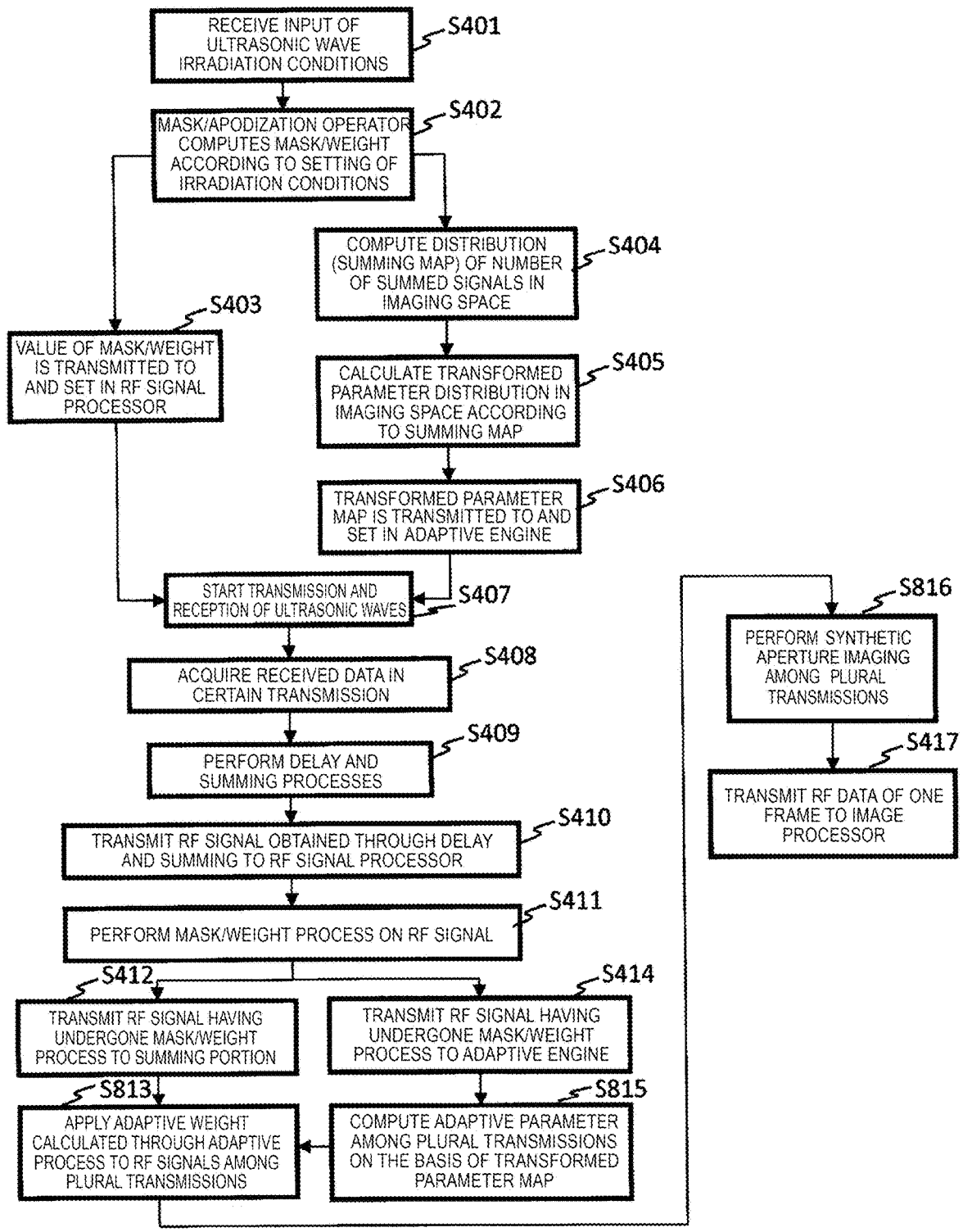

[Fig. 10]
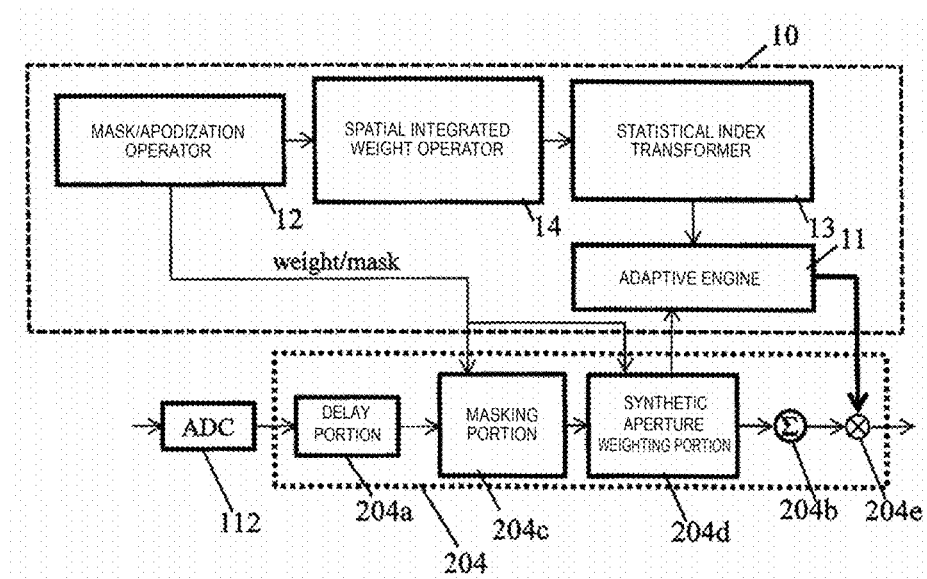

[Fig. 11]
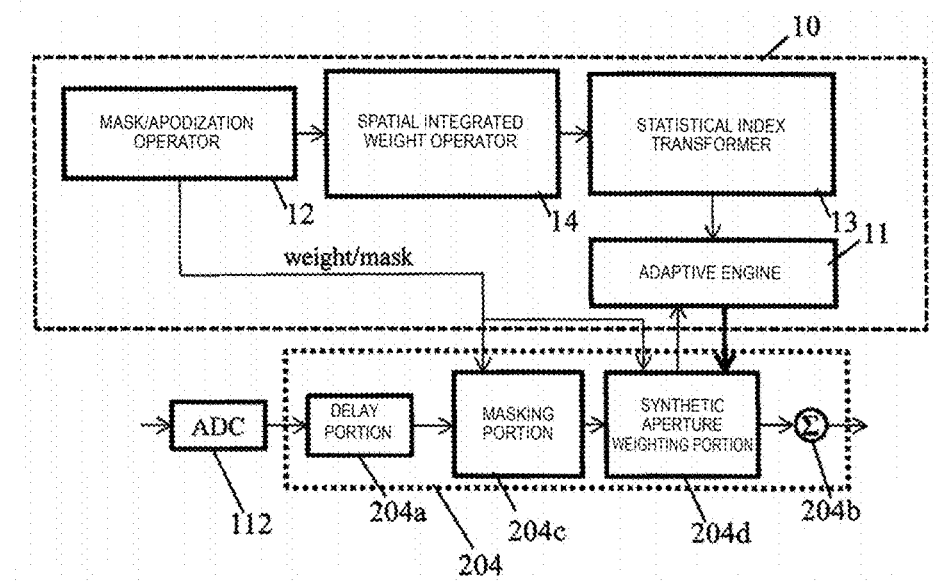

[Fig. 12]
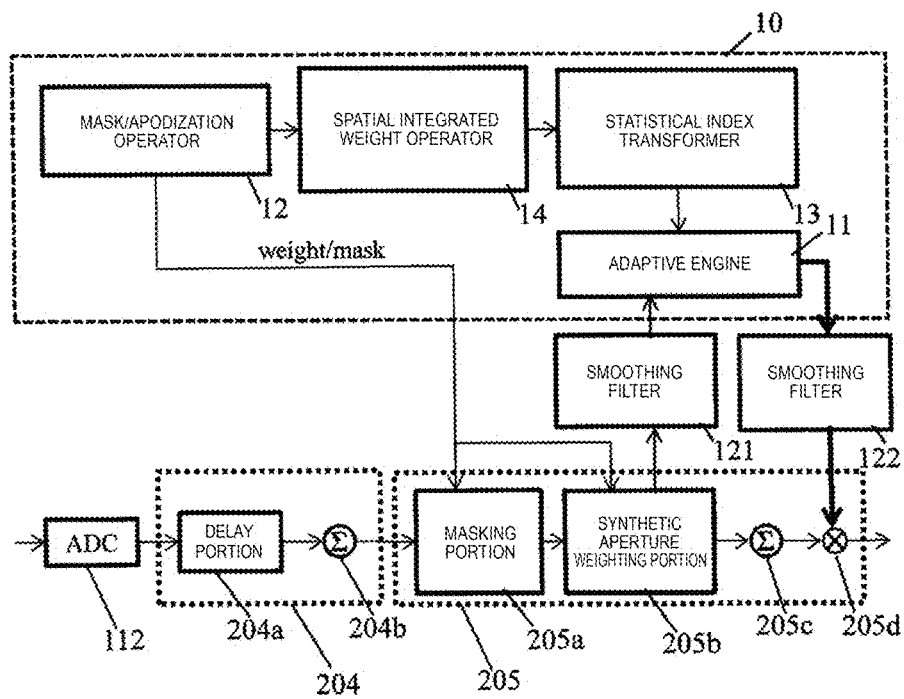

[Fig. 13]
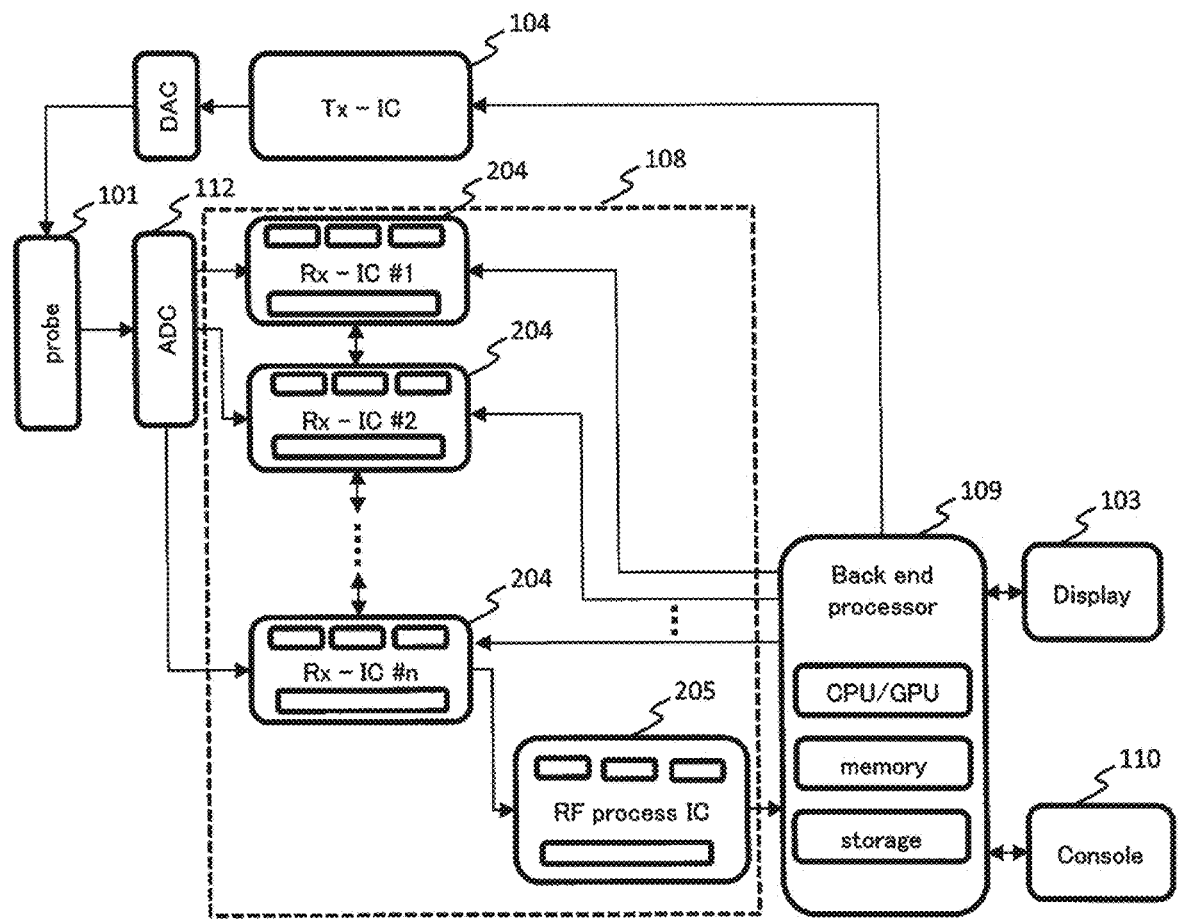

[Fig. 14]
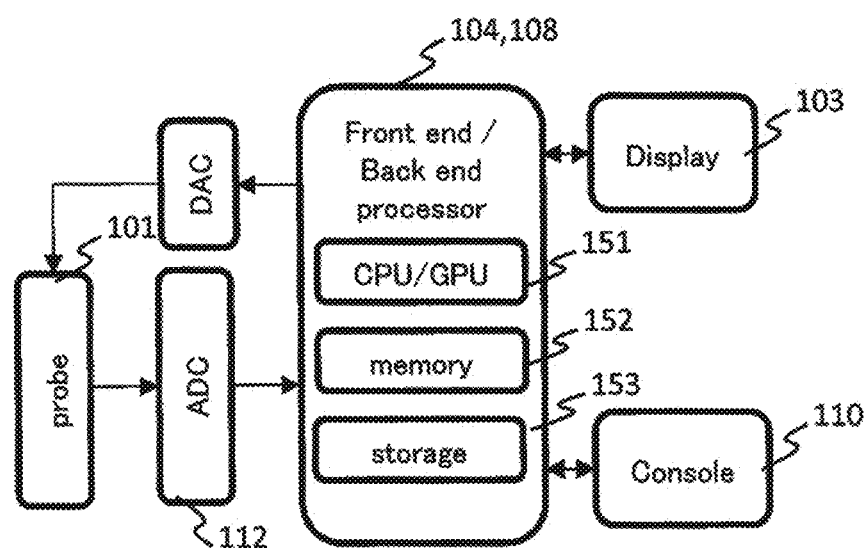

[Fig. 15A]
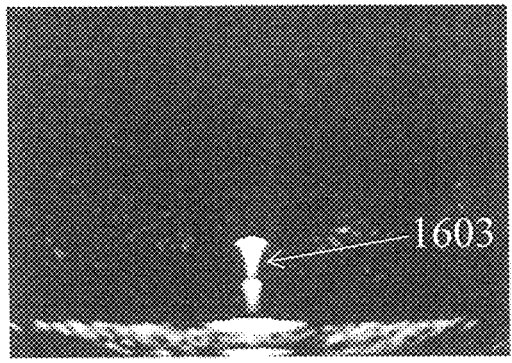
[Fig. 15B]
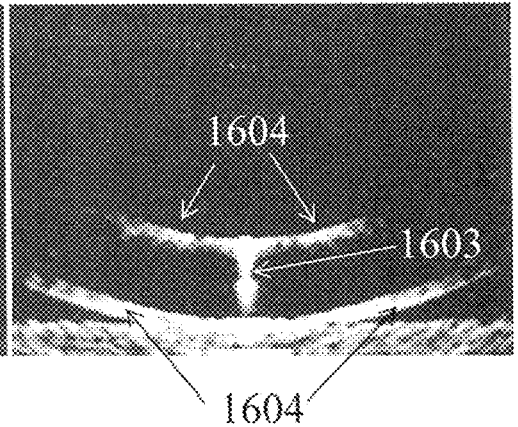

ULTRASONIC IMAGING DEVICE

TECHNICAL FIELD

The present invention relates to an ultrasonic imaging technique of capturing an image of the inside of a subject by using ultrasonic waves.

BACKGROUND ART

An ultrasonic imaging technique is a technique of imaging the inside of a subject including a human body in a noninvasive manner by using an ultrasonic wave (a sonic wave not intended to be listened, and, generally, a sonic wave with a high frequency of 20 kHz or more).

A method of transmitting an ultrasonic beam to a subject from an ultrasonic probe includes two types such as expanded type transmission of transmitting an ultrasonic beam which is spread in a fan shape, and focused type transmission in which a transmission focal point of an ultrasonic beam is disposed inside a subject, and the ultrasonic beam converges. Planar wave transmission without a focus is equivalent to a case where a focal position is placed at infinity in the above-described two transmission methods, and is included in at least any one of the two types of transmission.

Transmission and reception of an ultrasonic wave in an ultrasonic imaging apparatus are performed by an array having a finite opening diameter, and thus it is hard to improve a resolution in an azimuth direction due to the influence of diffraction of an ultrasonic wave occurring at an edge of an aperture portion. This problem can be solved if an infinitely long array is provided, but realization thereof is not easy in the current circumstances. Thus, in the recent years, in order to improve a resolution in an azimuth direction, a phasing technique effectively using received data in a channel domain has been actively examined, and a new phasing method such as adaptive beamformer or synthetic aperture imaging has been frequently reported.

Synthetic aperture imaging will be described briefly. First, an ultrasonic beam is transmitted, and an echo from a subject is received by an ultrasonic probe in which a plurality of elements are arranged. A delay time is applied to each received signal output from the plurality of elements such that the signals focus on a virtually present point, and are then summed together, and thus a phasing signal is obtained. The phasing signal is combined with another phasing signal obtained through transmission and reception performed once or more for the same point so as to be superimposed thereon, and thus synthetic aperture imaging is performed.

In the synthetic aperture imaging, phasing signals obtained through transmission and reception from different directions with respect to a certain point in an ultrasonic probe can be superimposed on each other, and thus it is expected that high resolution of a point image is achieved, and robustness against heterogeneity is given. Since a process gain is improved through the superimposition process, transmission in which the number of times of transmission of ultrasonic waves is reduced more than during normal times can be performed, and thus the synthetic aperture imaging can be applied to fast imaging.

There is a technique of reducing a clutter caused by acoustic artifact such as a side lobe or a grating lobe by using an adaptive process in an ultrasonic diagnosis image. For example, as the adaptive process, algorithms such as a coherent factor, minimum variance distortionless response (MVDR), amplitude and phase estimation (APES), and eigenspace minimum variance (ESMV) are known. The fundamental concept of the adaptive process in an ultrasonic diagnosis apparatus is that statistics of respective received signals are calculated, and only a probable signal is used. Consequently, it can be expected that an ultrasonic image from which the influence of a signal due to unnecessary acoustic artifact is excluded as much as possible is obtained.

PTL 1 discloses a technique regarding a phasing method including a synthetic (synthetic aperture imaging) process of a plurality of transmissions and removal of a clutter from an ultrasonic image using a coherence factor which is one type of adaptive signal processing, in an ultrasonic diagnosis apparatus.

PTL 2 discloses a technique of combining synthetic aperture imaging with an eigenspace beam forming method which is one type of adaptive process in an ultrasonic diagnosis apparatus.

CITATION LIST

Patent Literature

PTL 1: Specification of US2006/0173313A
PTL 2: Specification of US2014/0024943A

SUMMARY OF INVENTION

Technical Problem

As in PTL 1 or PTL 2, if adaptive signal processing is combined with a phasing method such as a synthetic aperture imaging process, a clutter in an ultrasonic image is reduced, and thus an ultrasonic image with a higher resolution can be expected to be generated.

On the other hand, in the adaptive signal processing, a signal is processed on the basis of the concept that statistics of respective received signals are calculated, and only a probable signal is used as described above, and thus there is a feature of being sensitive to the number of statistical samples used for calculation of statistics. In the related art, the number of bundled channels in phasing addition or the number of combinations in a combination between transmissions is substantially constant regardless of a position of an imaging point (pixel) in an image, and thus a nonlinear relationship between the number of statistical samples in the adaptive signal processing and a variable in an algorithm of the adaptive signal processing is not greatly important. Thus, a uniform value is used for a parameter sensitive to a statistical number in the adaptive signal processing.

In recent years, an imaging method positively using a focused transmission beam having a transmission focal point in a subject has been proposed. A shape of the focused transmission beam has a small beam width around the transmission focal point, and a large beam width in a region with a small depth near an ultrasonic probe, or, conversely, a region with a large depth. Thus, in a case where the focused transmission beam is used, the number of statistical samples for each pixel (imaging point) used for an adaptive process greatly changes depending on a depth. Therefore, in the related art, if uniformly processed various variables in an adaptive process algorithm, or an equation of the adaptive process algorithm is applied to an imaging method using the focused transmission beam without being changed, it is difficult to uniformly obtain a clutter reduction effect in the adaptive process with respect to the entire image.

An object of the present invention is to provide a technique capable of uniformly obtaining a clutter reduction effect using adaptive beam forming with respect to the entire image even in an imaging condition in which the number of bundled signals is greatly distributed in an ultrasonic image.

Solution to Problem

According to the present invention, there is provided an ultrasonic imaging apparatus including an ultrasonic probe that includes a plurality of ultrasonic elements transmitting an ultrasonic wave to a subject, receiving an ultrasonic wave from the subject, and outputting received signals; and a received signal processing unit that processes the received signals output from the ultrasonic probe. The received signal processing unit includes a summing unit that bundles the plurality of received signals for a predetermined imaging point or a plurality of signals obtained by processing the received signals, and a weighting unit that obtains a coherence value among the plurality of signals summed in the summing unit, and weights the plurality of signals before being summed in the summing unit or a signal obtained through summing in the summing unit, with a weight corresponding to the coherence value. The weighting unit weights the coherence value nonlinearly in a predetermined direction in the subject, and weights the plurality of signals before being summed in the summing unit or the signal obtained through summing in the summing unit by using the nonlinearly weighted coherence value.

Advantageous Effects of Invention

According to the present invention, it is possible to uniformly obtain a clutter reduction effect using adaptive beam forming with respect to the entire image even in an imaging condition in which the bundling number is greatly distributed in an ultrasonic image. Particularly, the present invention is useful in a case of using a transmission beam having a complex shape such as a focused transmission beam.

BRIEF DESCRIPTION OF DRAWINGS

FIG. 1 is a block diagram illustrating the entire configuration of an ultrasonic imaging apparatus of an embodiment.

FIG. 2 is an explanatory diagram illustrating a case where weighting is performed by using coherent values of signals summed in summing portions 204b and 205c of an embodiment.

FIG. 3 is a block diagram illustrating a configuration of a weighting unit 10 of a first embodiment.

FIG. 4 is a flowchart illustrating an operation of an ultrasonic imaging apparatus of the first embodiment.

FIG. 5A is an explanatory diagram illustrating a mask and a weight set by a mask/apodization operator 12 of the first embodiment, FIG. 5(b)FIG. 5B is an explanatory diagram illustrating a summing map generated by a spatial integrated weight operator 14, and FIG. 5C is an explanatory diagram illustrating a transformed parameter distribution generated by a statistical index transformer 13.

FIGS. 6A and 6B are explanatory diagrams illustrating the extent of superimposition of ultrasonic beams based on synthetic aperture imaging.

FIG. 7A is a graph obtained by extracting one line in a depth direction from the summing map in FIG. 5B. FIG. 7B is a graph illustrating a transformed parameter p(d) of which a value nonlinearly changes in a depth direction d. FIG. 7C is a graph illustrating a transform function p(n).

FIG. 8 is a block diagram illustrating a configuration of a weighting unit 10 of a second embodiment.

FIG. 9 is a flowchart illustrating an operation of an ultrasonic imaging apparatus of the second embodiment.

FIG. 10 is a block diagram illustrating a configuration of a weighting unit 10 of a third embodiment.

FIG. 11 is a block diagram illustrating a configuration of a weighting unit 10 of a fourth embodiment.

FIG. 12 is a block diagram illustrating a configuration of a weighting unit 10 of a fifth embodiment.

FIG. 13 is a block diagram illustrating a configuration of an ultrasonic imaging apparatus realized by hardware of a sixth embodiment.

FIG. 14 is a block diagram illustrating a configuration of an ultrasonic imaging apparatus realized by software of a seventh embodiment.

FIG. 15A illustrates an image obtained in an Example, and FIG. 15B illustrates an image obtained in a comparative example.

DESCRIPTION OF EMBODIMENTS

An ultrasonic imaging apparatus of an embodiment of the present invention will be described.

An ultrasonic imaging apparatus of an embodiment will be described with reference to FIGS. 1 and 2. FIG. 1 is a block diagram illustrating the entire configuration of the ultrasonic imaging apparatus, and FIG. 2 is an explanatory diagram illustrating the concept that weighting is performed according to a coherence value of a signal.

As illustrated in FIG. 1, the ultrasonic imaging apparatus of the present embodiment includes an ultrasonic probe 106, a received signal processing unit 108, and a transmission beamformer 104. The ultrasonic probe 106 includes ultrasonic array elements 101 in which a plurality of ultrasonic elements are arranged. Each of the ultrasonic elements receives a signal from the transmission beamformer 104, transmits an ultrasonic wave to a subject 100, receives an ultrasonic wave from the subject 100, and outputs a received signal. The received signal processing unit 108 processes a received signal output from the ultrasonic probe 106.

The received signal processing unit 108 includes a delay and sum unit 204 provided with a summing portion 204b which bundles a plurality of received signals for a predetermined imaging point, an RF signal processor 205 provided with a summing portion 205c which bundles a plurality of signals obtained by processing received signals, and a weighting unit 10. As illustrated in FIG. 2, the weighting unit 10 obtains coherence values of a plurality of signals to be summed in the summing portion (204b or 205c), and weights a plurality of signals before being summed in the summing portion (204 or 205) or signals after being summed in the summing portion (204 or 205) with weights (w1 to wk or Ψ) corresponding to the obtained coherence values. In a case where a signal is weighted according to a coherence value, weights of a plurality of signals having the same phase can be increased, and weights of a plurality of signals having different phases can be reduced. Therefore, a signal such as noise having a differing phase can be suppressed, and a summed signal can be generated by using an original received signal from an imaging point of a subject. Thus, it is possible to obtain a clutter reduction effect.

In this case, the weighting unit 10 nonlinearly weights coherence values in a predetermined direction (for example, a depth direction) in the subject. The weights (w1 to wk or Ψ) are obtained by using the nonlinearly weighted coherence values. Consequently, even in a case where the number of signals summed in the summing portion (204 or 205) nonlinearly differs depending on a position of an imaging point, weighting can be performed by taking into consideration the influence thereof. Therefore, it is possible to uniformly obtain a clutter reduction effect with respect to the entire image even in an imaging condition in which the number of bundled signals is greatly distributed in an ultrasonic image.

The ultrasonic imaging apparatus in FIG. 1 is configured to further include, in addition to the above constituent elements, a transmission/reception separation circuit (T/R) 107 which separates a transmission signal and a received signal from each other, an AD converter 112 which converts a received signal from an analog signal to a digital signal, an image processor 109 which generates image data by using a signal output from the received signal processing unit 108, a console 110 which receives input or the like of imaging conditions from an operator, and a control unit 111 which controls the entire operation, and an image display unit 103.

The received signal processing unit 108 includes the delay and sum unit 204 and the RF signal processor 205. The delay and sum unit 204 is provided with a delay portion 204a and the summing portion 204b as illustrated in FIG. 3. The delay portion 204a of the delay and sum unit 204 delays respective received signals in a plurality of ultrasonic elements of the ultrasonic probe 106 with respect to a plurality of reception focal points (imaging points) of a plurality of reception scanning lines, set in each transmission by the control unit 111. The summing portion 204b sums the delayed received signals together. Consequently, the delay and sum unit 204 generates a signal (low resolution image (LRI)) after phasing addition along reception scanning lines, that is, a low resolution RF signal after elements (channels) are bundled. The delay and sum unit 204 includes an RF signal memory 206, and can store a received channel RF signal and a generated low resolution RF signal for each transmission.

The generated low resolution RF signal is transmitted to the RF signal processor 205. A frame memory 207 may be provided in the RF signal processor 205, and the generated low resolution RF signal may be stored in the frame memory 207. In other words, a memory location in which the generated low resolution RF signal is temporarily stored may be any of the RF signal memory 206 of the delay and sum unit 204 and the frame memory 207 of the RF signal processor 205, but, preferably, the low resolution RF signal right after being generated is transmitted to and stored in the memory 207 of the RF signal processor 205 from the viewpoint of convenience of a reading process of the low resolution RF signal from the memory and a calculation process.

As illustrated in FIG. 3, the RF signal processor 205 includes a masking portion 205a, a synthetic aperture weighting portion 205b, and the summing portion 205c. The masking portion 205a reads low resolution RF signals stored in the RF signal memory 206 or the frame memory 207 with respect to a plurality of scanning lines for each transmission, and performs a masking process by using a mask set for each transmission, in order to determine which portion of low resolution RF data contributes to summing (bundling process. The synthetic aperture weighting portion 205b weights a low resolution RF signal in each transmission with a predetermined weight. Consequently, it is determined to what extent of weight RF data contributes to summing. The masked and weighted low resolution RF data is temporarily stored in the frame memory 207. Low resolution RF data in different transmissions is sequentially read from the memory, and is subject to a masking process and a weighting process. The summing portion 205c sums the weighted low resolution RF signal with pieces of data having the same reception focal point in different transmissions so as to perform synthetic aperture imaging, and thus generates high resolution RF data.

A synthetic aperture imaging process in the summing portion 205c may be performed right after masking and weighting are performed on low resolution RF data in each of a plurality of transmissions, and all pieces of low resolution RF data having undergone masking and weighting contributing to summing may be accumulated in the memory and are then collectively summed. In the former method, there is an advantage that the capacity of the memory can be minimized, and, in the latter method, there is an advantage that a synthetic aperture imaging process can be performed over a plurality of frames, and thus a degree of freedom of processing is increased. Thus, any method may be selected depending on purposes.

The weighting unit 10 may weight a plurality of received signals before being summed in the delay and sum unit 204 with the weights (w1 to wk) such that the received signals are summed in the delay and sum unit 204 as illustrated in FIG. 2, and may weight low resolution RF signals after being summed in the delay and sum unit 204 with the weight ($\Psi$). The weighting unit 10 may weight a plurality of low resolution RF signals before being summed in the RF signal processor 205 with the weights (w1 to wk) such that the low resolution RF signals are summed in the RF signal processor 205 as illustrated in FIG. 2, and may weight high resolution RF signals after being summed in the RF signal processor 205 with the weight ($\Psi$). Such a weighting process may be performed through combination of a plurality of processes.

Hereinafter, a configuration of the weighting unit 10 will be described in detail.

First Embodiment

In a first embodiment, a description will be made of a configuration in which the weighting unit 10 weights an RF signal having undergone synthetic aperture imaging in the RF signal processor 205 with an adaptive weight ($\Psi$). In the present embodiment, the weighting unit 10 generates the adaptive weight ($\Psi$) by taking into consideration that the number of signals undergoing synthetic aperture imaging for each reception focal point dynamically forms different spatial distributions depending on a difference in a position of the reception focal point.

First, a description will be made of the configuration of the weighting unit 10 with reference to FIGS. 1 and 3. The weighting unit 10 includes an adaptive engine 11 which obtains an adaptive weight, a mask/apodization operator 12, a statistical index transformer 13, and a spatial integrated weight operator 14. The adaptive engine 11 adaptively calculates a weight by using coherence (phase coincidence, signal similarity, or correlation degree) among low resolution RF signals bundled by the RF signal processor 205. The spatial integrated weight operator 14 calculates the number of low resolution RF signals to be bundled for each reception focal point, and obtains spatial distributions of the number of low resolution RF signals to be bundled on the basis of a position of the reception focal point in an ultrasonic image. The statistical index transformer 13 nonlinearly or linearly transforms a statistical index parameter (coherence value) used for calculation in the adaptive engine 11 on the basis of the spatial distributions of the number of low resolution RF signals to be bundled, obtained by the spatial integrated weight operator 14.

An operation of each portion of the weighting unit 10 will be described with reference to a flow in FIG. 4.

First, if an operator (examiner) inputs imaging conditions to the console 110, the control unit 111 outputs control signals indicating information regarding a probe condition, an ultrasonic irradiation condition, and a synthetic aperture imaging condition according to the imaging conditions (S401).

The mask/apodization operator 12 calculates a shape of an ultrasonic beam to be transmitted on the basis of the control signals, and sets a mask as illustrated in FIG. 5(a) on the basis of the shape of the ultrasonic beam. FIG. 5(a) illustrates an ultrasonic beam in focused transmission, in which a width of the ultrasonic beam is small around a transmission focal point, and a width of the ultrasonic beam is large in a shallow region close to the ultrasonic probe and a deep region. In FIG. 5(a), a white region is a region in which a weight is zero, that is, the RF signal processor 205 does not perform synthetic aperture imaging of signals, and a black region is a region in which the RF signal processor 205 performs synthetic aperture imaging of RF signals with a weight of 1. A gray region is a region in which a weight of 0 to 1 (a value which is greater than 0 and smaller than 1) is set, and synthetic aperture imaging of RF signals is performed with the set weight. The mask/apodization operator 12 sets, for example, the weight of zero (white) in the outside of the calculated outer shape of the ultrasonic beam, sets the gray region with the weight of 0 to 1 in a predefined shape in a plurality of predefined stages such that the weight gradually comes close to 1 from the contour of the ultrasonic beam toward the inside thereof, and sets the black region with the weight of 1 inside thereof (S402).

The mask/apodization operator 12 sets the region with the weight of zero (white) in FIG. 5(a) generated in step S402 in the masking portion 205a of the RF signal processor 205 as a mask, and sets the regions (gray and black) other than the region with the weight of zero and the weight values thereof in the synthetic aperture weighting portion 205b of the RF signal processor 205 (S403).

The mask/apodization operator 12 delivers the mask and the weights in FIG. 5(a) generated in step S402 to the spatial integrated weight operator 14. The spatial integrated weight operator 14 receives the synthetic aperture imaging conditions (FIGS. 6(a) and 6(b)) output from the control unit 111 in addition to the received mask and weights in FIG. 5(a). The spatial integrated weight operator 14 generates a map (hereinafter, referred to as a summing map) indicating a distribution of the summing number (n) of ultrasonic beams (received signals) 51 as illustrated in FIG. 5(b) in a case where synthetic aperture imaging of the ultrasonic beams (received signals) 51 is performed, on the basis of the synthetic aperture imaging conditions (S404). During summing, it is assumed that, in the black region in FIG. 5(a), the signals are summed with the weight of 1, and, in the gray region, the signals are summed with the weight values (0 to 1) for the respective regions. In the generated summing map in FIG. 5(b), white indicates that the number (n) of summed signals is zero, and, as a color comes close to black, the number (n) of summed signals becomes larger. As is clear from the summing map in FIG. 5(b), it can be seen that, since superimposition of the ultrasonic beams (received signals) 51 is almost absent or is small around the transmission focal point, a value of the summing number (n) is small (close to white), a value of the summing number (n) in regions of which a depth (d) is smallest and largest is large (black), and, in a region therebetween, the summing number (n) gradually becomes larger as a distance from the transmission focal point is increased. The spatial integrated weight operator 14 delivers the generated summing map (FIG. 5(b)) to the statistical index transformer 13.

The statistical index transformer 13 applies a transform a transform function which is nonlinear in the depth (d) direction, to the distribution of the summing number (n) in the summing map (FIG. 5(b)) so as to generate a transformed parameter distribution (FIG. 5(c)) in which the summing number is nonlinearly distributed in the depth direction (S405). This will be described in detail with reference to FIGS. 7(a) to 7(c). FIG. 7(a) is a graph obtained by extracting one line in the depth direction from the summing map in FIG. 5(b). The graph represents a function n(d), in which a transverse axis expresses the depth (d), and a longitudinal axis expresses the summing number (n). The statistical index transformer 13 applies a transform function p(n) of which a value nonlinearly changes according to a value of the summing number (n) as in FIG. 7(c) to the function n(d) representing a change of the summing number in the depth direction, so as to generate a transformed parameter p(d) (FIG. 7(b)) of which a value nonlinearly changes in the depth (d) direction. Regarding the transform function p(n), for example, a step function (a dashed line in FIG. 7(c)) in which the parameter (p) is zero up to a predetermined summing number (n), and the parameter (p) is an integer such as 1 at a summing number (n) which is equal to or larger than the predetermined summing number (n), a sigmoid function (a solid line in FIG. 7(c)) in which a value of the parameter (p) gradually comes close to a constant value in ranges in which the summing number (n) is large and small, or a raised cosine function may be used as the transform function p(n). The transform function p(n) is applied to the entire summing map (FIG. 5(b)), and thus a transformed parameter map (p) (FIG. 5(c)) of which a value nonlinearly changes in the depth direction is generated (S405).

The statistical index transformer 13 outputs and sets the generated transformed parameter map (p) (FIG. 5(c)) to and in the adaptive engine 11 (step S406).

Next, ultrasonic waves are transmitted and received in the ultrasonic probe 106 (S407). Respective received signals are acquired by the plurality of ultrasonic elements 105 in a single transmission, and the received signals are converted into digital signals in the AD converter 112 (S408). The digital signals obtained through conversion are stored in the RF signal memory 206 as channel RF data. The delay portion 204a of the delay and sum unit 204 sequentially reads the channel RF data from the RF signal memory 206, and delays a received signal in each ultrasonic element 105 such that the received signals are focused on respective reception focal points on a plurality of reception scanning lines set by the control unit 111. The summing portion 204b sums the plurality of delayed received signals together so as to generate a low resolution RF signal (S409). The low resolution RF signal as a result of being delayed and summed is stored in the RF signal memory 206. In a case where RF signals corresponding to the number of transmissions in which transmission synthetic aperture imaging is to be performed are stored in the RF signal memory 206, the control unit 111 transmits an RF signal obtained in each transmission in the low resolution RF signal memory 206 to the RF signal processor 205 (S410). Alternatively, the low resolution RF signal as a result of being delayed and summed is immediately transmitted to the RF signal processor so as to be stored in the frame memory 207 (S410). This is repeatedly performed in a plurality of transmissions. As described above, for convenience of sequentially reading the low resolution RF data from the memory in the RF signal processor and performing a calculation process, a low resolution RF signal is more preferably stored in the frame memory 207, but may be stored in the RF signal memory 206 due to a restriction of an apparatus configuration.

The masking portion 205a of the RF signal processor 205 applies the mask (the white region in FIG. 5(a)) set in step S403 to the low resolution RF signal in each transmission, transmitted from the delay and sum unit 204, and the synthetic aperture weighting portion 205b applies the weight values (the values of the gray and black regions in FIG. 5(a)) set in step S403 to the RF signals so as to perform weighting (S411).

In step S411, an RF signal after being masked and weighted is delivered to the summing portion 205c (S412). The summing portion 205c sums RF signals after being weighted, obtained in other transmissions and for the same reception focal point together (S413). Consequently, synthetic aperture imaging is performed among a plurality of transmissions, and thus a high resolution RF signal is generated. The generated high resolution RF signal is temporarily stored in the frame memory 207.

On the other hand, in step S411, the RF signal after being masked and weighted is also delivered to the adaptive engine 11 (S414).

The adaptive engine 11 obtains a coherence value of the RF signals between transmissions for each reception focal point by using the RF signal (s) after being masked and weighted in each transmission, and nonlinearly weights the coherence value according to a depth of the reception focal point. Specifically, a result of weighting the obtained coherence value with a corresponding parameter value of the reception focal point in the transformed parameter map (p) set in step S406 is used as an optimal adaptive weight Ψ for each reception focal point (S415). Specifically, an adaptive weight Ψ for a certain reception focal point is calculated according to the following Equation (1).

$$\Psi = \left( \frac{(s_1 + s_2 + \ldots + s_K)^2}{s_1^2 + s_2^2 + \ldots + s_K^2} \right)^p \quad (1)$$

Here, in Equation (1), $s_i$ indicates an RF signal which is obtained in an i-th transmission and has undergone masking and weighting. In addition, p indicates a parameter value of a certain reception focal point in the transformed parameter map (p). This calculation is performed for each of an imaging depth d, a sample point j in the depth direction, and a reception time point t, and Ψ or $s_i$ is a function of the depth d or the sample point j. Calculation is performed as in Ψ(d), Ψ(j), and Ψ(t) for each imaging depth, and inputs in the calculation are similarly $s_i(d)$, $s_i(j)$, and $s_i(t)$ for each depth.

The RF signal processor 205 includes a multiplication portion 205d as illustrated in FIG. 3, and performs weighting by multiplying the high resolution RF signal having undergone the synthetic aperture imaging for a predetermined reception focal point, calculated in step S413, by the adaptive weight Ψ for the same reception focal point obtained in step S415 (S416). The RF signal processor 205 includes the frame memory 207 as illustrated in FIG. 1, and the adaptive weight Ψ and the weighted high resolution RF signal are stored in the frame memory 207. The above steps S407 to S416 are repeatedly performed until high resolution RF signals of one frame are stored in the frame memory 207. If the RF signals of one frame are stored in the frame memory 207, the RF signals are transmitted to the image processor 109 (S417). Instead of transmitting signals to the image processor 109 for each frame, for convenience of a system, the signals may be weighted with the adaptive weight Ψ so as to be then sequentially transmitted to the image processor, and the signals of several frames may be collectively transmitted.

The image processor 109 performs backend image processing so as to generate an ultrasonic image (for example, a B-mode image) which is then output to and displayed on the image display unit 103. The image processor 109 may perform generation of various ultrasonic images, for example, a nonlinear captured image, an angiographic contrast image, a continuous wave Doppler image, a pulse Doppler image, a color flow image, and an acoustic wave image such as an elastography, or execution of an application, by using frame data sent from the frame memory 207.

Consequently, it is possible to uniformly obtain a clutter reduction effect using adaptive beam forming with respect to the entire image even in an imaging condition (for example, a focused transmission beam) in which the number (n) of summed RF signals during synthetic aperture imaging is greatly distributed in an ultrasonic image, and thus to generate an ultrasonic image in which noise is reduced and which has a high resolution.

In the first embodiment, in steps S414 and S415, the adaptive engine 11 calculates the adaptive weight Ψ by using an RF signal weighted by the synthetic aperture weighting portion 205b of the RF signal processor 205 in step S411 of the flow in FIG. 4 with a fixed weight in FIG. 5(b) set by the mask/apodization operator 12. As mentioned above, the adaptive engine 11 calculates the adaptive weight by using the RF signal weighted with the fixed weight, and thus the adaptive weight can be calculated by using the RF signal from which an unnecessary component is removed to some extent by the fixed weight. Therefore, it is possible to obtain an advantage that artifact or clutter reduction performance is improved.

In the first embodiment, the step of weighting an RF signal with the fixed weight in step S411 may be omitted. In this case, the adaptive engine 11 calculates the adaptive weight Ψ by using the RF signal not having undergone any process, or the RF signal having undergone only masking. As a result, a weighting function may be a linear function. This is because nonlinear calculation includes linear calculation as a special example thereof. In other words, even if a weighting function is a linear function or an integer as a result of processing in the present invention, this is included in an embodiment of the present invention.

The transformed parameter map in FIG. 5(c) is generated through nonlinear weighting in the depth direction (d) as in FIGS. 7(a) to 7(c), but nonlinear weighting is not necessarily performed in the depth direction (d), and the transformed parameter map may be generated through nonlinear weighting in any other directions.

Second Embodiment

In the first embodiment, the RF signal processor 205 weights an RF signal having undergone synthetic aperture imaging with the adaptive weight (Ψ), but, in the second embodiment, the RF signal processor 205 weights RF signals not having undergone synthetic aperture imaging with adaptive weights (w1 to wk), respectively. In the present embodiment, the weighting unit 10 generates the adaptive weights (w1 to wk) by taking into consideration that the number of signals undergoing synthetic aperture imaging for each reception focal point is distributed depending on a reception focal point.

FIG. 8 illustrates a configuration of the weighting unit 10 of the second embodiment, and FIG. 9 illustrates a flow showing an operation thereof. As illustrated in FIG. 8, a configuration of the weighting unit 10 of the second embodiment is the same as the configuration in the first embodiment illustrated in FIG. 3 except that the adaptive engine 11 obtains the adaptive weights (w1 to wk) for respective RF signals. The second embodiment is different from the first embodiment in that the synthetic aperture weighting portion 205b includes a multiplication portion 205e calculating the adaptive weights (w1 to wk) for respective RF signals as illustrated in FIG. 2.

As illustrated in FIG. 9, steps S401 to S412, and S414 are performed in the same manner as in the first embodiment. The adaptive engine 11 obtains the adaptive weights (w1 to wk) as follows by using RF signals in respective transmissions received in step S414 (S815).

Signals which are input to the adaptive engine 11 are RF signals s1 to sk obtained in k transmissions. The adaptive engine creates a covariance matrix R(t) by using the following Equation (2). Here, t is a reception time point, but a function of the imaging depth d or the sample point j may be used instead of a function of t. In Equation (2), * indicates a conjugate complex number. In Equation (2), $s_i$ indicates an RF signal which is obtained in an i-th transmission and has undergone masking and weighting. E[ ] indicates an expected value.

$$R(t) = E[s(t)s^H(t)] = E\left\{\begin{pmatrix} s_1(t)s_1^*(t) & s_1(t)s_2^*(t) & \cdots & s_1(t)s_K^*(t) \\ s_2(t)s_1^*(t) & s_2(t)s_2^*(t) & \cdots & s_2(t)s_K^*(t) \\ \vdots & \vdots & \ddots & \vdots \\ s_K(t)s_1^*(t) & s_K(t)s_1^*(t) & \cdots & s_K(t)s_K^*(t) \end{pmatrix}\right\} \quad (2)$$

An adaptive weight vector w(t) may be computed on the basis of the following Equation (3) according to, for example, an MVDR method by using the covariance matrix. In addition, p is a value of the transformed parameter map (p) set in step S406. The normal adaptive weight vector w(t) corresponds to a case of the exponent p=1. Through this process, a nonlinear weight corresponding to the number of summed signals can be applied to the weight w(t).

$$w(t) = \left(\frac{R^{-1}(t)}{a^H R^{-1}(t) a}\right)^p \quad (3)$$

In order to remove numerical value instability, a size of a diagonal matrix applied to the correlation matrix (covariance matrix R(t)) is changed as in Equation (4). Here, p is a value of the transformed parameter map (p) set in step S406. The second term on the right side of Equation (4) is a diagonal matrix I for providing numerical value stability to the adaptive process. A size of the second term also depends on a size of a matrix. In other words, it is necessary to change a coefficient applied to I depending on a difference in the summing number K. Therefore, it is possible to minimize a variation in a process result by multiplying the diagonal matrix I by the function α(p) determined according to a value of the parameter map (p) as in Equation (4). The simplest example of α(p) may include a form of α=βp multiplied by any integer β.

$$R_{new}(t) = R(t) + \alpha(p)I$$

or $$R_{new}(t) = (1-\alpha(p))R(t) + \alpha(p)I \quad (4)$$

In Equation (3), a which is a steering vector is an inclination relative to a direction of an input vector (s), and is expressed as in Equation (5) on the basis of a phase relationship of each transmission number n (=1, 2, . . . , N).

$$a = [\exp\{\psi_1(\theta, f)\}, \exp\{\psi_2(\theta, f)\}, \ldots, \exp\{\psi_N(\theta, f)\}] \quad (5)$$

In Equation (5), θ indicates a phase shift amount when a case where phase rotation is zero among respective transmission numbers is set to θ=0, and f is a frequency of an ultrasonic wave. Generally, at θ=0, a=[1, 1, . . . , 1] may be expressed by a vector having all elements of 1, and a direction of this vector is set as a steering vector direction.

The adaptive engine 11 may calculate the adaptive weight vector w(t)=[w1, w2, . . . , wk] corresponding to the transmission numbers 1 to k through the above-described process (S815). The calculated adaptive weights (w1 to wk) are delivered to the synthetic aperture weighting portion 205b.

The synthetic aperture weighting portion 205b includes the multiplication portion 205e performing weighting on each RF signal, and performs weighting by multiplying the k RF signals by the adaptive weights (w1 to wk), respectively (S813). The k weighted RF signals are summed together by the summing portion 205c (S816). Step S417 is performed in the same manner as in the first embodiment.

Consequently, it is possible to uniformly obtain a clutter reduction effect using adaptive beam forming with respect to the entire image even in an imaging condition (for example, a focused transmission beam) in which the number (n) of summed RF signals during synthetic aperture imaging is greatly distributed in an ultrasonic image, and thus to generate an ultrasonic image in which noise is reduced and which has a high resolution.

A calculation method for an adaptive weight is not limited to the MVDR method, and w(t) may be calculated by using various weight generation processes such as an APES method, a MUSIC method, and an ESMV method.

A covariance matrix for performing sub-array averaging may be used as in the following Equations (6) to (8). The sub-array number L or the magnitude of an average window width S in a time direction is also an index. In K signals $s_i(t)$ as shown in Equation (6), a sub-array matrix is expressed as in Equations (7) and (8). Here, L indicates a size of the sub-array. N indicates the average number in the time direction, and takes an average of matrices with a time width of ±S centering on a certain point t. Sub-array averaging or time averaging is performed, so that a signal can be smoothed, and thus it is possible to obtain more robust output. In this case, the extent of smoothing of a signal is calculated as a function ε(p) or γ(p) as in Expression (10) or Equation (11) by using the transformed parameter map (p), and thus highly robust weight calculation is possible.

$$s(t) = [s_1(t), s_2(t), \ldots, s_K(t)] \quad (6)$$

$$\tilde{s_l}(t) = [s_{K-l-1}(t), s_{K-l-2}(t), \ldots s_{K-l-K}(t)]^T \quad (7)$$

$$\tilde{R}(t) = \frac{1}{N(K-L+1)} \sum_{s=-S}^{S} \sum_{l=1}^{K-L+1} \tilde{R}_{SUB1}(t) \quad (8)$$

$$N = 2S \quad (9)$$

-continued $$L < \varepsilon(p) \quad (10)$$

$$S = \gamma(p) \quad (11)$$

In the second embodiment, in steps S414 and S815, the adaptive engine 11 calculates the adaptive weights w1 to wk by using RF signals weighted by the synthetic aperture weighting portion 205b of the RF signal processor 205 in step S411 of the flow in FIG. 9 with a fixed weight in FIG. 5(b) set by the mask/apodization operator 12. As mentioned above, the adaptive engine 11 calculates the adaptive weights by using the RF signals weighted with the fixed weight, and thus the adaptive weight can be calculated by using the RF signals from which an unnecessary component is removed to some extent by the fixed weight. Therefore, it is possible to obtain an advantage that artifact or clutter reduction performance is improved. In the second embodiment, the step of weighting RF signals with the fixed weight in step S411 may be omitted. In this case, the adaptive engine 11 calculates the adaptive weights w1 to wk by using the RF signals not having undergone any process, or the RF signals having undergone only masking.

Third Embodiment

In the third embodiment, a description will be made of a configuration in which the weighting unit 10 weights an RF signal obtained as a result of summing in the delay and sum unit 204 with the adaptive weight (Ψ). In the present embodiment, the weighting unit 10 generates the adaptive weight (Ψ) by taking into consideration that the number of delayed and summed signals is distributed depending on a position of a reception focal point.

As illustrated in FIG. 10, in the third embodiment, the same masking portion 204c and delay and sum weighting portion 204d as the masking portion 205a and the synthetic aperture weighting portion 205b of the first embodiment are disposed between the delay portion 204a and the summing portion 204b of the delay and sum unit 204. A multiplication portion 204e is disposed in the rear stage of the summing portion 204b.

The mask/apodization operator 12 generates, as a mask for the masking portion 204c and a weight for the delay and sum weighting portion 204d, a mask in which a small number of elements is summed in a shallow location in consideration of the influence of diffraction, and the number of elements is increased as a depth increases, and a weight expressed by a hanning function or a raised cosine function in a diameter direction. Consequently, the masking portion 204c masks a plurality of received signals which are delayed by the delay portion 204a such that the received signals are focused on reception focal points on reception scanning lines, and the delay and sum weighting portion 204d weights the received signals.

The spatial integrated weight operator 14 generates a map (summing number map) indicating a distribution of the summing number (n) by using the mask and the weights generated by the mask/apodization operator 12 in the same manner as in the first embodiment. The statistical index transformer 13 generates a transformed parameter map on the basis of the summing number map in the same manner as in the first embodiment.

The adaptive engine 11 receives the plurality of received signals weighted by the delay and sum weighting portion 204d, calculates a coherent value according to, for example, Equation (1), and nonlinearly weights the coherence value with p of the transformed parameter map so as to obtain the adaptive weight Ψ.

The summing portion 204b of the delay and sum unit 204 sums the plurality of received signals weighted by the synthetic aperture weighting portion 205b so as to obtain an RF signal. The multiplication portion 204e of the delay and sum unit 204 performs weighting by multiplying the RF signal obtained through summing in the summing portion 204b by the adaptive weight Ψ obtained by the adaptive engine 11.

Since the adaptive weight Ψ is weighted with the summing number map, synthetic aperture imaging of weighted RF signals is performed by the RF signal processor 205, and thus it is possible to uniformly obtain a clutter reduction effect using adaptive beam forming with respect to the entire image even in an imaging condition (for example, in a case where the steering accuracy is high, such as a 2D array or a phased array probe having a shallow focus and a large aperture) in which the number (n) of summed received signals during delaying and summing is greatly distributed in an ultrasonic image, and thus to generate an ultrasonic image in which noise is reduced and which has a high resolution.

Fourth Embodiment

In the fourth embodiment, a description will be made of a configuration in which the weighting unit 10 weights received signals before being summed in the delay and sum unit 204 with the adaptive weights (w1 to wk). In the present embodiment, the weighting unit 10 generates the adaptive weights (w1 to wk) by taking into consideration that the number of delayed and summed signals is distributed depending on a position of a reception focal point.

As illustrated in FIG. 11, in the fourth embodiment, the same masking portion 204c and delay and sum weighting portion 204d as in the third embodiment are disposed between the delay portion 204a and the summing portion 204b of the delay and sum unit 204. The delay and sum weighting portion 204d includes the multiplication portion 205e as illustrated in FIG. 2.

The mask/apodization operator 12 generates a mask for the masking portion 204c and a weight for the delay and sum weighting portion 204d in the same manner as in the third embodiment. The masking portion 204c masks a plurality of received signals which are delayed by the delay portion 204a such that the received signals are focused on reception focal points on reception scanning lines, and the delay and sum weighting portion 204d weights the received signals.

The spatial integrated weight operator 14 generates a map (summing number map) indicating a distribution of the summing number (n) in the same manner as in the third embodiment. The statistical index transformer 13 generates a transformed parameter map in the same manner as in the third embodiment.

The adaptive engine 11 receives the plurality of received signals weighted by the delay and sum weighting portion 204d, and obtains the adaptive weights (w1 to wk) which are nonlinearly weighted with p of the transformed parameter map according to Equations (2) to (5) of the second embodiment.

The delay and sum weighting portion 204d of the delay and sum unit 204 weights k received signals weighted by the masking portion 204c with the adaptive weights (w1 to wk), respectively. The summing portion 204b sums the weighted received signals together so as to obtain an RF signal.

Since the adaptive weights (w1 to wk) are weighted with the summing number map p, synthetic aperture imaging of weighted RF signals is performed by the RF signal processor 205, and thus it is possible to uniformly obtain a clutter reduction effect using adaptive beam forming with respect to the entire image even in an imaging condition (for example, in a case where the steering accuracy is high, such as a 2D array or a phased array probe having a shallow focus and a large aperture) in which the number (n) of summed received signals during delaying and summing is greatly distributed in an ultrasonic image, and thus to generate an ultrasonic image in which noise is reduced and which has a high resolution.

Fifth Embodiment

The fifth embodiment has the same configuration as the configuration illustrated in FIG. 3 of the first embodiment as illustrated in FIG. 12, but is different from the first embodiment in that a smoothing filter 121 which smooths a plurality of signals which are input to the adaptive engine 11, and a smoothing filter 122 which smooths the adaptive weight $\Psi$ output from the adaptive engine 11 are disposed between the adaptive engine 11 and the RF signal processor 205.

In an adaptive process performed by the adaptive engine 11, a value of a signal is determined for each sample point of the signal, but coherence of actual signals occurs with a larger time scale. Specifically, coherence changes with a time scale corresponding to a wavelength (about ten times larger than an interval (sampling cycle) of sample points of a signal) of an ultrasonic wave. Thus, the smoothing filters 121 and 122 are disposed, so that coherence can be detected with higher accuracy, and thus image quality can be further improved.

In FIG. 12, the smoothing filters 121 and 122 are disposed in the configuration of the first embodiment, but are not limited to the first embodiment, and the smoothing filters 121 and 122 processing an input signal and an output signal to and from the adaptive engine 11 may also be disposed in the configurations of the second to fourth embodiments. As a smoothing algorithm, a simple algorithm such as movement averaging may be used, and low pass filtering after being thinned-out, FIR sample interpolation, spline interpolation, or the like may be used.

Sixth Embodiment

FIG. 13 illustrates an example of a hardware configuration in which the received signal processing unit 108 of the ultrasonic imaging apparatus of the first to fifth embodiments is formed of integrated circuits (ICs) as the sixth embodiment. The delay and sum unit 204 of the received signal processing unit 108 is formed of a plurality of delay and sum ICs. The plurality of delay and sum ICs are connected to each other, and received signals output from a plurality of ultrasonic elements are processed by any of the delay and sum ICs. The RF signal processor 205 is formed of a single received signal processing IC.

The delay and sum ICs and the RF signal processing IC may be configured by using a field-programmable gate array (FPGA) or an application specific integrated circuit (ASIC).

In the configuration example illustrated in FIG. 13, the image processor 109 includes a central processing unit (CPU) or a graphics processing unit (GPU), a memory, and a storage unit, and an operation of the image processor 109 is configured to be realized by the CPU or GPU executing a program stored in the memory.

Seventh Embodiment

FIG. 14 illustrates an example in which the transmission beamformer 104 and the received signal processing unit 108 of the ultrasonic imaging apparatus of the first to fifth embodiments are formed of a CPU or a GPU, or a combination 151 of the CPU and the GPU, a memory 152, and a storage unit 153 as the seventh embodiment. A program stored in the memory 152 is executed by the CPU or the GPU 151, and thus an operation of the transmission beamformer 104 and operations of the delay and sum unit 204 and the RF signal processor 205 of the received signal processing unit 108 are configured to be realized by software.

Example

FIG. 15(*a*) illustrates an image 1601 obtained through transmission and reception in the ultrasonic imaging apparatus of the first embodiment as an Example. FIG. 15(*b*) illustrates an image 1602 obtained through transmission and reception in an ultrasonic apparatus of a comparative example (in a case where the weight $\Psi$ is not applied among transmissions).

It can be seen that, in the image 1602 of the comparative example, clutters 1604 are present near a true image 1603, but, in the image 1601 of the Example, the clutters 1604 are suppressed, and thus only the true image 1603 is displayed.

REFERENCE SIGNS LIST

11 ADAPTIVE ENGINE
12 MASK/APODIZATION OPERATOR
13 STATISTICAL INDEX TRANSFORMER
14 SPATIAL INTEGRATED WEIGHT OPERATOR
100 SUBJECT
101 ULTRASONIC ARRAY ELEMENT
103 IMAGE DISPLAY UNIT
104 TRANSMISSION (Tx.) BEAMFORMER
106 ULTRASONIC PROBE
107 TRANSMISSION/RECEPTION SEPARATION CIRCUIT (T/R)
108 RECEIVED (Rx.) SIGNAL PROCESSOR
109 IMAGE PROCESSOR
110 CONSOLE
111 CONTROL UNIT
112 AD CONVERTER (ADC)
204 DELAY AND SUM UNIT
205 RF SIGNAL PROCESSOR

The invention claimed is:

1. An ultrasonic imaging apparatus comprising:
an ultrasonic probe that includes a plurality of ultrasonic elements transmitting an ultrasonic wave to a subject, receiving an ultrasonic wave from the subject, and outputting received signals; and
a received signal processing circuit that processes the received signals output from the ultrasonic probe,
wherein the received signal processing circuit includes
a summing circuit that sums the received signals for a predetermined imaging point or a plurality of signals obtained by processing the received signals to produce a plurality of summed signals, and
a weighting circuit that obtains a coherence value among the plurality of summed signals, and weights the plurality of signals before being summed in the summing circuit or a signal obtained through summing in the summing circuit, with a weight corresponding to the coherence value, wherein
- the weighting circuit weights the coherence value nonlinearly in a predetermined direction in the subject, and weights the plurality of signals before being summed in the summing circuit or the signal obtained through summing in the summing circuit by using the nonlinearly weighted coherence value, and
- the weighting circuit includes a distribution operator that calculates a number of the plurality of summed signals having undergone phasing addition in the summing circuit based on shapes of transmitted ultrasonic beams and superimposition of the ultrasonic beams during transmission synthetic aperture imaging.

2. The ultrasonic imaging apparatus according to claim 1, wherein
the summing circuit is a delay and sum portion, delays the received signals output from the plurality of ultrasonic elements such that the received signals are focused on the predetermined imaging point, and then sums the received signals together.

3. The ultrasonic imaging apparatus according to claim 1, wherein
the weighting circuit obtains an adaptive weight by using the nonlinearly weighted coherence value, and weights the plurality of signals before being summed in the summing circuit or the signal obtained through summing in the summing circuit by using the adaptive weight.

4. The ultrasonic imaging apparatus according to claim 1, wherein
the weighting circuit includes a smoothing processor that smooths the plurality of signals summed in the summing circuit, and obtains the weight with which the plurality of signals before being summed in the summing circuit or the signal obtained through summing in the summing circuit is weighted, by using the plurality of signals smoothed by the smoothing processor and the nonlinearly weighted coherence value.

5. The ultrasonic imaging apparatus according to claim 1, wherein
the summing circuit is a synthetic aperture imaging portion, and sums signals having undergone a plurality of number of times of phasing addition, obtained for a same imaging point through a plurality of transmissions and receptions.

6. The ultrasonic imaging apparatus according to claim 5, wherein
the nonlinear weighting is defined based on a distribution of superimposition of ultrasonic waves transmitted in the plurality of transmissions.

7. The ultrasonic imaging apparatus according to claim 6, wherein
the weighting circuit uses a value obtained by raising the coherence value to a power of a parameter which is nonlinear in a depth direction, as the nonlinearly weighted coherence value.

8. The ultrasonic imaging apparatus according to claim 1, wherein
the predetermined direction is a depth direction of the subject.

9. The ultrasonic imaging apparatus according to claim 8, wherein
the distribution operator of the weighting circuit obtains a distribution of the number of the plurality of summed signals, and
the weighting circuit further includes a parameter transformer that transforms the distribution of the number of the plurality of summed signals into a parameter distribution by weighting the distribution of the number of the plurality of summed signals nonlinearly in the predetermined direction, wherein
the weighting circuit calculates the weight with which the plurality of signals before being summed in the summing circuit or the signal obtained through summing in the summing circuit is weighted, based on the parameter distribution.

10. The ultrasonic imaging apparatus according to claim 9, wherein
the weighting circuit further includes a mask operator that generates a mask for excluding signals outside an ultrasonic beam shape based on the shapes of the transmitted ultrasonic beams, wherein
the received signal processing circuit sums signals inside the ultrasonic beam shape selected by the mask with the summing circuit.

11. The ultrasonic imaging apparatus according to claim 9, wherein
the parameter transformer performs calculation of multiplying a weight function by a function indicating the distribution of the number of summed signals by using the weight function which nonlinearly changes according to the magnitude of the number of summed signals, in order to weight the distribution of the number of summed signals nonlinearly in the predetermined direction.

12. The ultrasonic imaging apparatus according to claim 9, wherein
the weighting circuit weights an inner region of the ultrasonic beam shape in a plurality of stages, and calculates the number of summed signals having undergone the phasing addition in the summing circuit by taking into consideration the weighting inside the ultrasonic beams.

13. The ultrasonic imaging apparatus according to claim 12, wherein
the received signal processing circuit weights signals summed in the summing circuit by using a weight with which the inner region of the ultrasonic beam shape is weighted in a plurality of stages, and then further weights the signals by using the nonlinearly weighted coherence value.

* * * * *